United States Patent
Ali bin M. Abdullah

(10) Patent No.: US 8,415,094 B2
(45) Date of Patent: Apr. 9, 2013

(54) PROTEIN-FREE GAMETE AND EMBRYO HANDLING AND CULTURE MEDIA PRODUCTS

(76) Inventor: Jaffar Ali bin M. Abdullah, Kuala Lumpur (MY)

( * ) Notice: Subject to any disclaimer, the term of this patent is extended or adjusted under 35 U.S.C. 154(b) by 940 days.

(21) Appl. No.: 12/340,475

(22) Filed: Dec. 19, 2008

(65) Prior Publication Data
US 2009/0226879 A1 Sep. 10, 2009

Related U.S. Application Data

(60) Provisional application No. 61/015,764, filed on Dec. 21, 2007.

(51) Int. Cl.
*A01N 1/02* (2006.01)

(52) U.S. Cl.
USPC ................................. 435/2; 435/325; 435/383

(58) Field of Classification Search .............. 435/2, 325, 435/383; 35/2, 325, 383
See application file for complete search history.

(56) References Cited

U.S. PATENT DOCUMENTS

| | | | | |
|---|---|---|---|---|
| 5,328,844 | A | * | 7/1994 | Moore ........................... 435/405 |
| 5,641,647 | A | * | 6/1997 | Fischer et al. ................. 435/69.1 |
| 6,140,121 | A | * | 10/2000 | Ellington et al. .............. 435/374 |
| 6,391,654 | B1 | * | 5/2002 | Bateman ........................ 436/518 |
| 7,892,725 | B2 | * | 2/2011 | Graham et al. .................... 435/2 |
| 2006/0148074 | A1 | * | 7/2006 | Gorfien et al. ................. 435/325 |
| 2007/0184529 | A1 | * | 8/2007 | Etcheverry et al. ........... 435/69.1 |
| 2008/0227136 | A1 | * | 9/2008 | Pla et al. .......................... 435/29 |
| 2010/0143877 | A1 | * | 6/2010 | Rozeboom ........................ 435/2 |
| 2011/0229585 | A1 | * | 9/2011 | Kaiser ............................ 424/643 |

FOREIGN PATENT DOCUMENTS

| WO | WO 2005/108555 | 11/2005 |
|---|---|---|
| WO | WO 2005/120576 | 12/2005 |

OTHER PUBLICATIONS

Bryant et al. J. Nat. Cancer Inst. (1962) 26: 239-252.*
Evans et al. Experimental Cell Res. (1964) 36: 439-74.*
Sigma-Aldrich Product Information Sheet for Methyl Cellulose (Jun. 3, 1997) downloaded from www.sigma-aldrich.com Sep. 24, 2011) 5 pages.*
Perlman, D. TCA Manual (1976) 2(3): 383-386.*
Ali et al. Human Reproduction (2000) 15(1): 145-156.*
Quinn (1994), "Use of co-culture with cumulus cells in insemination medium in human in vitro fertilization (IVF)." J. Assist. Reprod. Genet.11: 270-277.
Saito et al. (1994), "Cumulus mass maintains embryo quality." Steril. 62: 555-558.
Schramm and Bavister (1996), "Development of in-vitro-fertilized primate embryos into blastocysts in a chemically defined, protein-free culture medium." Hum. Reprod.11: 1690-1697.
Serta et al. (1997), "Outcome of human embryos conceived and cleaved in protein-free culture conditions." Fertility and Sterility 68 Suppl. 1: S214-S215.
Spindle (1995), "Beneficial effect of taurine on mouse zygotes developing in protein-free culture medium." Theriogenology 44: 761-772.
Staessen et al. (1998), "Controlled comparison of commercial media for human in-vitro fertilization:Menezo B2 medium versus Medi-Cult universal and BM1 medium." Hum. Reprod. 13 2548-2554.
Stewart et al. (1995), "Methylcellulose protects the ability of anchorage-dependant cells to adhere following isolation and holding in suspension." Biotechniques 19(4): 598-604.
Stoll et al. (1996), "Systematic improvement of a chemically defined protein-free medium for hybridoma growth and monoclonal antibody production." J. Biotechnology 45: 111-123.
Tesarik et al. (1988), "The role of cumulus cell-secreted proteins in the development of human sperm fertilizing ability: implications in IVF." Hum. Reprod. 3: 129-132.
Truyen et al. (1995), "There is nothing permanent except change. The emergence of new viral diseases." Vet. Microbiol. 43: 103-122.
Van Os et al. (1991), "The influence of contamination of culture medium with hepatitis B virus on the outcome of in vitro fertilization pregnancies." Am. J. Obstet. Gynecol. 165: 152-159.
Vidlakova et al. (1972), "Relationship of serum antioxidative activity to tocopherol and serum inhibitor of lipid peroxidation." Chim. Acta 36, 61-66.
Wayner et al. (1987), "The relative contribution of vitamin F, mate, ascorbate and proteins to total peroxyl radical-trapping antioxidant activity of human blood plasma." Biochim. Biophys. Acta 924: 408-419.
Weinberg et al. (2002), "Legal, financial, and public health consequences of HIV contamination of blood and blood products in the 1980s and 1990s." Ann. Intern. Med. 136: 312-319.
Widdowson and Dickerson (1964). "Chemical composition of the body," In: Comar, L.C. and Brommer, F. (eds.), Mineral Metabolism, Academic Press: New York, vol. II, Part A, p. 13.
Zang et al. (1995), "Production of Recombinant Proteins in Chinese Hamster Ovary Cells Using a Protein-Free Cell Culture Medium." Biotechnology 13: 389-392.
Gajdova, et al., Delayed Effects of Neonatal Exposure to Tween 80 on Female Reproductive Organs in Rats, Food Chem Toxicol., 31(3):183-90 (1993).
Kitchin, et al., Further Development of Rodent Whole Embryo Culture: Solvent Toxicity and Water Insoluble Compound Delivery System, Toxicology, 30:45-57 (1984).
Lemeire, et al, The antibiotic streptomycin assessed in a battery of in vitro tests for reproductive toxicology, Toxicology in Vitro, 21:1348-1353 (2007).
Pitt, et al, Evaluation of Various Toxicants in Rabbit Whole-Embryo Culture using a New Morphologically-Based Evaluation System, Teratology, 59:102-109 (1999).
Karabulut, et al., Investigation of Developmental Toxicity and Teratogenicity of Macrolide Antibiotics in Cultured Rat Embryos, Anatomia Histologia Embryologia, 37:369-375 (2008).
Bismut, et al., Role of serine biosynthesis and its utilization in the alternative pathway from glucose to glycogen during the response to insulin in cultured foetal-rat hepatocytes, Biochem. J. 276:577-582 (1991).

(Continued)

*Primary Examiner* — Susan Hanley

(74) *Attorney, Agent, or Firm* — McDonnell Boehnen Hulbert & Berghoff LLP

(57) ABSTRACT

This invention discloses a substantially protein-free cell culture solution for assisted reproductive technologies and methods of use thereof.

50 Claims, No Drawings

OTHER PUBLICATIONS

Devreker, et al., Amino acids promote human blastocyst development in vitro, Human Reproduction, 16:749-756 (2001).

Lane, et al., Mitrochondrial Malate-Aspartate Shuttle Regulates Mouse Embryo Nutrient Consumption, The Journal of Biological Chemistry, 28:18361-18367 (2005).

Gardner, et al,. Amino Acids and Ammonium Regulate Mouse Embryo Development in Culture, Biology of Reproduction, 48:377-385 (1993).

Ali (1997), "Formulation of a protein-free culture system for the culture of human embryos: preliminary findings and pregnancies," in Programme and abstract book of the 16th Annual Scientific Meeting of the Fertility Society of Australia, Dec. 2-4, 1997, Adelaide, Australia, pp. 34-35.

Ali (2000), "Investigation into the nutrient requirement of the human embryos: Successful formulation and clinical trial of a novel protein-free embryo culture medium." Emirates Med J. 18: 195-202.

Ali (2004), "Generation of viable human embryos in a protein-free embryo culture (ART-7b) medium enhances clinical pregnancy rate and prevents disease transmission in assisted reproduction." Middle East Fertil Soc. J. 9: 118-127.

Ali et al. (1998), "Term deliveries from human embryos conceived in a novel culture medium devoid of added protein." Middle East Fertil. Soc. J. 3: 40.

Ali et al. (1993), "Effect of culture systems on mouse early embryo development." Hum. Reprod. 8: 1110-1114.

Almagor et al. (1996), "Pregnancy rates after communal growth of pre-implantation human embryos in vitro." Fertil. Steril. 66: 394-397.

Balakier (1993), "Tripronuclear human zygotes: the first cell cycle and subsequent development." Hum. Reprod. 8: 1892-1897.

Barber (1961), "Inhibition of lipid peroxide formation by vertebrate blood serum." Arch. Biochem. Biophys. 92: 38-43.

Barnes et al. (1995), "Blastocyst development and pregnancy after in vitro maturation of human primary oocytes, intracytoplasmic sperm injection and assisted hatching." Hum. Reprod. 10: 3243-3247.

Bavister (1995), "Culture of pre-implantation embryos: facts and artifacts." Hum. Reprod. Update 1:91-148.

Biggers et al. (1997), "Polyvinyl alcohol and amino acids as substitutes for bovine serum albumin in culture media for mouse pre-implantation embryos." Hum. Reprod. Update 3: 125-135.

Boyers et al. (1987), "The effect of polyploidy on embryo cleavage after in vitro fertilization in humans." Fertil. Steril. 48: 624-627.

Canesco et al. (1992), "Embryo density and medium volume effects on early marine embryo development." J. Assist. Reprod. Genet. 9: 454-457.

Caro and Trounson (1986), "Successful fertilization, embryo development, and pregnancy in human in vitro fertilization (IVF) using a chemically defined culture medium containing no protein." Journal of in Vitro Fertilization and Embryo Transfer 3(4): 215-217.

Carrillo et al. (1998), "Improved clinical outcomes for in vitro fertilization with delay of embryo transfer from. 48 to 72 hours after oocyte retrieval: use of glucose- and phosphate-free media." Fertil. Steril. 69: 329-334.

Centers for Disease Control (1985), "Fatal degenerative neurologic disease in patients who received pituitary derived human growth hormone." MMWR Morb Moral Wkly Rep 34: 359-60, 365-6.

Cholewa and Whitten (1965), "Development of 2-cell mouse embryos in the absence of a fixed nitrogen source." J. Reprod. Fertil. 22: 553-555.

Cockle et al. (1989), "The TRH-related peptide by pyroglutamylglutamylprolinamide is present in human semen." FEBS Lett. 252: 13-7.

Craven et al. (1997), "AIDS: safety, regulation and the law in procedures using blood and blood products." Med. Sci. Law 37: 215-227.

Dandekar and Glass (1990), "Development of two-cell mouse embryos in protein-free and protein-supplemented media." J. In Vitro Fertil. Embryo Transfer 7: 107-113.

De Mouzon and Lancaster (1997), "World collaborative report on in vitro fertilization. Preliminary data for 1995." J. Assist. Reprod. Genet. (suppl.) 14: 250S-265S.

Drakakis et al. (1996), "The in vitro development of mouse embryos beyond the blastocyst stage into the hatching and outgrowth stage using different energy sources." J. Assist Reprod. Genet. 13: 786-792.

Du and Wales (1993), "Effect of culture from the zygote stage on the metabolism of glucose and glutamine by 2-cell embryos and blastocysts recovered from. outbred or H female mice." Reprod. Fertil. Dev. 5: 555-565.

Esmonde et al. (1994), "Creutzfeldt-Jakob disease and lyophilised dura mater grafts: report of two cases." J. Neurol. Neurosurg. Psychiat. 56: 999-1000.

Evatt (2006), Infectious disease in the blood supply and the public health response. Semin. Hematol. 43(2 Suppl 3): S4-9.

Gardner (1994), "Mammalian embryo culture in the absence of serum or somatic cell support." Cell Biol. Int. 18: 1163-1179.

Gardner et al. (1998), "Culture of viable human blastocysts in defined sequential serum-free media." Hum. Reprod. (suppl.) 13: 148-160.

Gardner et al. (1998), "A prospective randomized trial of blastocyst culture and transfer in in-vitro fertilization." Hum. Reprod. 13: 3434-3440.

Green et al. (1996), "A possible mechanism of action for fertilization promoting peptide, a TRH-related tripeptide that promotes capacitation and fertilizing ability in mammalian spermatozoa." Mol. Reprod. Dev, 45: 244-52.

Heye et al. (1994) "Creutzfeldt-Jakob disease and blood transfusion." Lancet 343: 298-299.

International Search Report for International Application No. PCT/US2008/087818, International Publication No. WO 2009/086191, mailed Mar. 30, 3009.

Kane et al. (1997), "Peptide growth factors and preimplantation development." Hum. Reprod. Update 3: 137-157.

Keen (1995), "The culture of rat myeloma and rat hybridoma cells in a protein-free medium." Cytotechnology 17: 193-202.

Kemmann (1998), "Creutzfeldt-Jakob disease (CJD) and assisted reproductivetechnology (ART)." Hum. Reprod. 13: 1777.

Keshavjee et al. (2001), "Medicine betrayed: hemophilia patients and HIV in the US." Soc. Sci. Med. 53: 1081-1094.

Kovár et al. (1987), "Iron Compounds at high Concentrations Enable Hybridoma Growth in a Protein-free Medium." Biotechnology Letters 9(4): 259-264.

Lane and Gardner (1997), "Non-essential amino acids and glutamine decrease the time of the first three cleavage divisions and increase compaction of mouse zygotes in vitro." J. Assist Reprod. Genet. 14: 398-403.

Li et al. (1996), "Development of rabbit zygotes into blastocysts in defined protein-free medium and offspring born following culture and embryo transfer." Theriogenology 47: 1103-1113.

Lighten et al. (1998), "Routine addition of human insulinlike growth factor-1 ligand could benefit clinical in-vitro fertilization culture." Hum. Reprod. 13: 3144-3150.

Loutradis et al. (1992), "Successful pregnancy in human IVF using BSA as a protein source in the transfer medium." Assist. Reprod. Technol. Androl. 3: 233-238.

Mehta and Kicssling (1990), "Development potential of mouse embryos conceived in vitro and cultured in ethylenediaminetetraacetic acid with and without amino acids or serum." Biol. Reprod. 43: 600-606.

Milne (1965), "Renal pharmacology." Annu. Rev. Pharmacol. 5: 119-36.

Moessner and Dodson (1993), "The role of growth factors and proteins in media for in vitro fertilization." Assist. Reprod. Rev. 3: 63-67.

Palermo et al. (1992), "Pregnancies after intracytoplasmic injection of a single spermatozoon into oocyte." Lancet. 340: 17-18.

Paria and Dey (1990), "Pre-implantation embryo development in vitro: cooperative interactions among embryos and the role of growth factors." Proc. Natl. Acad. Sci. USA 87: 4756-4760.

Paria et al. (1991), "Epidermal growth factor-specific protein tyrosine phosphorylation in pre-implantation embryo development." Biol. Reprod. 45: 711-718.

Parinaud et al. (1998), "Human sperm capacitation and in vitro fertilization in a chemically defined and protein-free medium (SMART1)." Human Reproduction, vol. 13, No. 9, pp. 2579-2582.

Parinaud et al. (1998), "Use of plant enzyme preparation (coronase) instead of hyaluronidase for cumulus cell removal before intracytoplasmic sperm injection." Hum. Reprod. 13: 1933-1935.

Parinaud et al. (1999), "Use of a medium devoid of 5 any human or animal compound (SMART2I) for embryo culture in intracytoplasmic sperm injection." J. Assist. Reprod. Genet. 16: 13-16.

Poiley (1960), "A systematic method of breeder rotation for non-inbred laboratory animal colonies." Proc. Anim. Care Panel 10; 159-166.

* cited by examiner

PROTEIN-FREE GAMETE AND EMBRYO HANDLING AND CULTURE MEDIA PRODUCTS

The present invention claims priority to Norwegian Patent Application No. 20076604, filed in the Norwegian Patent Office on Dec. 21, 2007, the entire contents of which are incorporated herein by reference.

FIELD OF THE INVENTION

The present invention relates to protein-free media (PFM) specialized and optimized for human reproduction and fertility programs. The substantially protein-free media products described herein are useful in preventing transmission of protein-bound pathogens including inter alia and in particular prions to patients undergoing infertility treatment, to newborns conceived from Assisted Reproduction Technologies (ART) and to workers in these areas of endeavor, specifically relating to application in human ART.

BACKGROUND OF THE INVENTION

Conventional commercially-available embryo culture media for human ART procedures contain human serum albumin (HSA) obtained from human blood and tissue sources. In some laboratories bovine serum albumin (BSA) is also used as a source of protein in human embryo culture procedures (Loutradis et al., 1992; Quinn, 1994), similarly obtained from blood and tissue sources from cows. The efficiency of media containing HSA and BSA was reported to be similar (Staessen et al., 1998). The use in culture medium of protein obtained from donors (human or bovine) has the potential to transmit diseases to patients undergoing assisted conception treatment. The generation of viable human embryos in a chemically-defined culture system (devoid of added protein or albumin, or animal or human-derived protein extract) beginning from oocyte collection, followed by sperm washing, insemination, fertilization up to the cleaved embryo stage and finally embryo transfer has not been described, although chemically-defined media for mouse, rabbit and primates have been reported in recent years (Spindle, 1995; Li et al., 1996; Schramm and Bavister, 1996). Previous claims of a chemically defined protein-free medium (PFM) for human application, in fact, were not truly protein-free, because the sperm meant for fertilization was still prepared in medium that contained serum proteins (Mohr & Trounson, 1986; Serta and Kiessling 1997 (Abst); Parinaud et al. 1999). A totally protein-free media for ART procedures thus has not been described hitherto.

The availability of a chemically defined medium used for generating viable early cleavage stage human embryos is needed in the art to ensure the safety of patients undergoing assisted reproduction treatment by avoiding the use of potentially hazardous donor protein. Concern over possible transmission of pathogenic diseases, in particular viral diseases, such as human acquired immunodeficiency disease syndrome (AIDS) and hepatitis, or Creutzfeldt-Jakob disease (CJD) transmitted by prions or others in blood-derived products has led a number of providers of healthcare services in the area of ART worldwide to seek alternative(s) to donor protein for their embryo culture and handling procedures.

The transmission of a deadly viral disease (AIDS) to hemophiliacs through blood-derived products is well documented (See, for example, Craven et al., 1997, *Med. Sci. Law* 37: 215-227; Keshavjee et al., 2001, *Soc. Sci. Med.* 53: 1081-1094; Weinberg et al., 2002, *Ann. Intern. Med.* 136: 312-319; Evatt, 2006, *Semin. Hematol.* 43: S4-9). Human growth hormone extracted from the pituitary was found to be capable of transmitting CJD to humans (Esmonde et al., 1994) and human gonadotropin injections could also transmit CJD from person to person (CDC, 1985). CJD can be transmitted through blood (although the titer of CJD prions is low in blood; Heye et al., 1994). In the past an epidemic of hepatitis B occurred in about 200 IVF patients that received embryos cultured in medium containing pooled sera contaminated with hepatitis B virus (van Os et al., 1991). Recently the scientific community was confronted with the dilemma of having to inform their patients that a commercial preparation of a culture medium used for embryo culture and handling may be contaminated with albumin donated by a person who later died of CJD (Kemmann, 1998).

There are a number of reports of development of mouse blastocysts from zygote and cleaved stages in a protein-free medium. The earliest reports include those of Brinster (1965) and, Cholewa and Whitten (1970) who used polyvinylpyrrolidone (PVP), which is a high molecular weight colloid, as a lubricant and for increasing the viscosity of the medium. Subsequent to this work a number of other workers have successfully cultured mouse as well as other mammalian embryos in protein-free media (Dandekar and Glass, 1990; Spindle, 1995; Li et al., 1996; Schramm and Bavister, 1996). In recent years, in addition to PVP, polyvinyl alcohol (PVA) (Bavister, 1995) has also been used to replace serum protein in culture medium. For example, Biggers et al. (1997) investigated the effect of replacing bovine serum albumin (BSA) with polyvinyl alcohol (PVA) and/or amino acids on mouse zygote development. They observed that PVA could not be substituted completely for BSA in the mouse embryo culture medium. The effect of PVA on rate of blastocyst development was only slightly less than with BSA but the rate of partial hatching was significantly less. Substitution of BSA with PVA lowered the overall response but did not lead to major perturbations.

In addition to its many biological roles, serum proteins confer useful physical attributes such as lubrication and viscosity in the culture medium. Increased viscosity and lubrication in the culture medium is required for ease of handling and manipulation of the embryo and to prevent it from adhering to the walls of the culture dish and embryo transfer catheters. The incorporation of PVP and PVA merely serve to duplicate the physical attributes of serum proteins. However, PVP and PVA are not sources of fixed nitrogen and they do not perform the various biological roles of protein. In addition, the teratological properties of PVP and PVA have not been fully examined, which make their use in human therapeutic assisted reproduction questionable (Gardner and Lane, 1998a).

Some investigators have attempted to generate viable human embryos in a protein-free culture system, most recently Serta et al. (1997) and Parinaud et al. (1998a). However Serta and co-workers (1997) prepared their spermatozoa for insemination by swim-down through a column of BSA (although subsequent culture was performed in a protein-free medium). These workers achieved a pregnancy rate of 31% (n=45) some of which have proceeded to term with the birth of normal offspring. Parinaud et al. (1998a) obtained fertilizations with spermatozoa prepared in a protein-free medium when insemination was performed in the same medium. However the resultant zygotes were cultured in BM1 medium, and although this reference did not specify whether their BM1 medium contained protein, a previous publication from the same group suggested BM1 medium contained 1% HSA (Parinaud et al., 1998b).

Some workers have shown that replacement of serum protein with a single antioxidant and chelator such as EDTA (Mehta and Kiessling, 1990; Serta et al., 1997) does not impair fertilization and cleavage of viable embryos in the mouse and human. However Serta et al. (1997) suggested that the embryo transfer catheter be rinsed extensively with the protein-free medium, which implies the tendency of embryos to stick to the inner wall of embryo transfer catheter. Serum protein also has a role in maintaining pH in culture medium (Moessner et al., 1993). Beside its role as a nutrient in biological systems, protein has a number of other roles such as a chain-breaking antioxidant and a chelator of metal ions (Barber, 1961; Vidlakova et al., 1972; Wayner et al., 1987).

The physiological functions of albumin and plasma proteins in general are well documented. The role of albumin in preventing membrane peroxidation indicates a direct role in membrane stability. It is involved in capillary membrane permeability and in osmoregulation. Albumin provides 80% of the total colloid osmotic pressure in plasma. Albumin is involved in the transport of carbon dioxide and acts as a pH buffer; albumin accounts for the greatest (95%) portion of the non-bicarbonate buffer value of plasma. Proteins also serve as a source of energy. Deaminated alanine is pyruvate, which can be either converted to acetyl-CoA or glucose and glycogen. Albumin may help solubilize lipids and transports hormones, vitamins and metals. It serves as reservoirs for the release and use of these components.

Any attempt at substituting serum albumin in culture medium should therefore take into consideration these in vivo roles and physical attributes which are useful for embryo handling and manipulation in vitro. A single component may not fulfill all the functions of serum protein.

Although protein-free media that supports development of a number of animal species has been described previously, no such protein-free media has been successfully used in humans, nor could such media be presumed to support or be optimal for human embryo development. Thus there exists a distinct need for a defined, protein-free growth medium especially adapted for human ART and IVF.

BACKGROUND OF THE RELATED ART

There are previously known putatively "protein-free" media for treating and cultivating mammalian cells, particularly cells from rodents (mice, rats, guinea pigs, etc.) but also for fertilization, embryo development and pregnancy in humans for in vitro fertilization.

Caro et al. have described one such "protein-free" medium for human application; however they were not able to overcome the need for proteins in the sperm preparation medium because proteins are required to induce capacitation of the sperm without which the sperm will not acquire the capacity to penetrate and/or fertilize the egg. Thus, Caro and co-worker's media system is not completely protein-free. Likewise, Serta et al. (1997; abstract) and Parinaud et al. (1998a, abstract; 1999) have also described "protein-free" media for human ART but they, like Caro et al. (1986) before them used proteins in at least one stage of their culture system.

Washing sperm previously prepared with medium containing added proteins as described in these references does not remove contaminating infectious agents with complete certainty, especially viruses and prions. In addition, this is also disadvantageous because it subjects the spermatozoa to unnecessary stressful washing conditions, and can impose excessive demands on manpower and resources.

"Protein-free" media for growth of mammalian or particularly human cells outside the IVF context has been disclosed, inter alia, in Kovár et al., 1987, *Biotechnology Letters*, vol. 9 no. 4, p. 259-264 "Iron Compounds at high Concentrations Enable Hybridoma Growth in a Protein-free Medium"; Keen, 1995, *Cytotechnology*, vol. 17: 193-202 "The culture of rat myeloma and rat hybridoma cells in a protein-free medium"; Stoll et al., 1996, *J. Biotechnology*, vol. 45, p. 111-123 "Systematic improvement of a chemically defined protein-free medium for hybridoma growth and monoclonal antibody production." This work is related specifically to monoclonal antibody production and does not disclose adapting such media for IVF or ART uses. Other publications disclosing protein-free growth media, but not adapted or suitable for human IVF procedures are: Zang et al., 1995, *Biotechnology*, vol. 13, p. 389-392, "Production of Recombinant Proteins in Chinese Hamster Ovary Cells Using A Protein-Free Cell Culture Medium"; and International patent application Publication no. WO 2005/120576 A2.

SUMMARY OF THE INVENTION

The present invention relates to novel protein-free embryo culture media formulations for retrieval of the human egg (i. Flushing medium), handling and storage of spermatozoa (ii. Gamete Handling Medium), fertilization of the human egg (iii. Embryo Culture Medium), gamete and embryo handling (iv. Gamete and Embryo Handling Medium), and as well as development of the resulting zygote in culture (v. Embryo Culture Medium) through 1 to 2 cleavage cycles for human application in the treatment and alleviation of sub-fertility and infertility using ART procedures. The present invention includes the formulation of a single medium solution that can replace and/or be used as a replacement/medium for all of the above novel media solutions. The substantially protein-free media of the invention are distinct from the protein-free media (termed ART-7 and ART-7b series therein) previously reported by the same inventor (Ali, 1997; Ali et al., 2000). In previous reports, the inventor has described the systematic investigation that led to the formulation of three precursor media, namely, ART-1, ART-2 and ART-3. In the same report the inventor has described how the substantially protein-free media series ART-7 and ART-7b evolved from the ART-1 medium. The embryos generated by intra-cytoplasmic sperm injection (ICSI) in the substantially protein-free ART-7 and ART-7b media series was successfully used to treat 11 of 21 (52.4%) women of 39 years of age or lower to achieve clinical pregnancies. The formulation of ART-1, ART-7 and ART-7b media series has not been disclosed. The present invention provides substantially protein-free media that has been formulated from, but is different from, the precursor ART-3 medium. The development of the precursor ART-3 medium, but not its composition, has been described by the inventor (Ali, 1997; Ali et al., 2000).

In exemplary embodiments of this invention, a series of substantially protein-free media are specifically disclosed, termed the PFM-11 series herein. These media have the specific advantage of being of uniform composition devoid of potentially hazardous non-uniform biological components that may harm gametes and embryos, and could potentially transmit deadly presently known and hitherto unknown diseases to the patients undergoing ART treatment, the babies conceived through such treatment and to healthcare workers involved in ART treatment procedures, as well as to comply with rigorous new norms and regulations governing in vitro fertilization techniques and methods.

The completely defined nature of the substantially protein-free media formulations according to the present invention also is useful in facilitating research into pre-implantation embryo metabolism that was previously hampered due to the undefined nature and non-uniform composition of currently available embryo culture media formulations. The quality of day 2 human embryos generated in these substantially protein-free media (PFM) series using the continuous ultramicrodroplet (cUMD) culture technique was statistically comparable to or better than embryos that developed in control commercial media formulations containing serum proteins. The PFM media were not toxic to human spermatozoa. Fertilization and subsequent development of human embryos by conventional IVF and intra-cytoplasmic sperm injection (ICSI) was comparable to controls.

The substantially protein-free media of this invention also are suitable for use in substantially protein-free human embryo culture and handling media and will ensure that protein-bound diseases are not transmitted to patients and newborns. The substantially protein-free media of the invention can be stored frozen at −20° C. for up to 2 years without loss of efficacy.

The present invention has successfully overcome the need for added donor proteins in the culture system and provides a substantially protein-free media system for human ART application that utilizes substantially protein-free media products beginning from egg retrieval, sperm preparation, insemination, fertilization, culture of resultant embryo and embryo transfer. This feature advantageously distinguishes the media of this invention from previously described "protein-free" culture systems, which utilized protein-containing media products at some point during the procedure and were thus not completely protein-free. As a consequence, these prior culture media can be contaminated with infectious agents and may face possible regulatory restrictions. The compositions, ranges, preferred ranges and particular specifications of the various components of the present invention are set forth herein.

The present invention is the product of studies on the effect, tolerance and determination of optimal levels of individual components such as amino acids, antioxidants and chelators, osmolytes, vitamins, nutrients and alternate energy sources that could substitute in part the various roles of protein in vivo and in vitro and which exemplifies the functions of proteins in various protein-free handling media (e.g. sperm and oocyte handling media, and ICSI medium) and embryo culture media of this invention that is free of donor serum proteins. The optimal concentrations of the mentioned components were utilized to formulate a number of embryo culture media. Subsequently the best of these media showing optimal embryo development and significantly higher blastocyst hatching rate were identified and further refined to support human embryo development in the absence of added serum proteins. The substantially protein-free media of the invention are capable of supporting fertilization of human oocytes with spermatozoa prepared in the same medium. The resultant zygotes subsequently developed in the substantially protein-free medium to form viable early cleavage-stage human embryos. The transfer of these embryos led to normal pregnancies and live births.

The present invention thus successfully provides media useful throughout IVF/ART procedures (egg retrieval, sperm preparation, insemination, fertilization, culture of resultant embryo and embryo transfer) that overcome the need for added proteins in the culture system.

DETAILED DESCRIPTION OF CERTAIN EMBODIMENTS OF THE INVENTION

The present invention provides a series of nutrient solutions generically referred to as embryo handling and culture media that are devoid of any protein or protein-like components. These media are useful in the fertilization of human eggs and the subsequent development of fertilized eggs for up to 2 to 6 days outside the body in vitro. These nutrient solutions are called "embryo culture media". In addition to IVF and ART, other methodologies and techniques where it would be advantageous to use substantially protein-free nutrient growth media include stem cell technology and therapy, cell/tissue regeneration and transplantation treatment procedures. The skilled worker will appreciate how to adapt the media set forth herein for such uses.

As disclosed in further detail below, use of the substantially protein-free media of this invention for human gametes and embryos increased the efficacy of IVF and ART. For example, the clinical pregnancy rate obtained using conventional IVF with substantially protein-free (PFM-11) media is increased to 50% (14 of 28) in all age groups and up to 53.8% (14 of 26) in women below 40 years of age; when compared to currently available embryo media containing proteins (33% pregnancies for all age groups combined, as cited in Ali, 2004). The ICSI clinical pregnancy rate with substantially protein-free media of this invention is likewise increased to 46.2% (12 of 26) in all age groups and up to 54.5% (12 of 22) in women below 40 years of age. This difference is statistically significant in favor of the present substantially protein-free media, indicating that the substantially protein-free media of this invention is at least equivalent to (and can be superior to) currently available commercial protein-containing medium currently available in the market. The number of babies born from embryos generated in the PFM-11 media by conventional IVF was 12 and by IC SI, 12. The babies born from embryos generated in the PFM-11 of the invention are apparently normal, intelligent, talkative and active (according to parental reports). These statistical data were produced from a sample of at least 24 children from such births.

As used herein, the term "protein-free," "essentially protein-free" and "substantially protein-free" is intended to mean that the media was prepared using non-protein containing components (as described in further detail herein) and that no protein or protein-containing components were added to the media.

Exemplary embodiments of the present invention include a series of substantially protein-free media termed the PFM-11 series. These media series have a range of specific media products, namely:
1. Substantially Protein-Free Flushing Medium
2. Substantially Protein-Free Gamete (Sperm) Handling Medium
3. Substantially Protein-Free Gamete (Oocyte/Embryo) Handling medium
4. Substantially Protein-Free Embryo Culture Medium These media are used according to the methods set forth below, which are intended to illustrate the use of these media but are not limiting to any additional uses of the media, inter alia, in IVF or ART methods known to those with skill in the art. In developing the media of the invention in experiments as set forth herein, each procedure was performed in parallel using conventional protein-containing media and exemplary PFM of the invention.

Human Spermatozoa Preparation

Male patients produced human semen by masturbation. Spermatozoa were prepared by the standard swim-up technique and occasionally with density gradient centrifugation. In the density gradient procedure, the recovered pellet was washed twice and resuspended in culture medium. Spermatozoa preparations were made using test or control media as appropriate. Specifically, spermatozoa for ICSI or IVF were prepared in the substantially protein-free (PFM-11) medium for the experiments on the effect of protein deficiency on embryo development. The harvested spermatozoa were incubated under gaseous phase of 5% $CO_2$ in air at 37° C. until use.

Ovarian Stimulation and Oocyte Retrieval

Ovarian stimulation was induced by subcutaneous injections of gonadotrophin-releasing hormone agonist (Buserelin; Suprefact; Hoescht, Frankfurt, Germany) starting in the mid-luteal phase until menstruation or down-regulation was achieved. Down-regulation was considered to have been achieved when endometrial thickness was 4 mm or less, and when blood estradiol, progesterone and LH levels reached baseline values. Injections of follicle stimulating hormone (FSH; Metrodin; Serono, Rome, Italy) were administered for three days to initiate recruitment of follicles. Thereafter, human menopausal gonadotrophin (Pergonal 500; Serono, Rome, Italy) was administered according to the response of the patient to stimulate follicular development. Ovulation was induced by an injection of a 10,000 IU of human chorionic gonadotrophin (hCG; Pregnyl; Organon, Oss, Holland) after achieving follicular size of 16 mm or more. Oocyte retrieval (OR) was performed 36 h later by ultrasound guided vaginal aspiration.

Insemination and Culture Techniques

In Vitro fertilization (IVF)

Oocytes were individually inseminated with motile spermatozoa in micro-droplets of equilibrated culture medium at a concentration of 100,000/mL under equilibrated and embryo tested mineral oil (M8410, Sigma Chemicals, and USA). The inseminated oocytes were cultured in an atmosphere of 5% $CO_2$ in air at 37° C. The following morning the oocytes were denuded with denuding pipettes (Stripper®, MidAtlantic Diagnostics, USA).

Intracytoplasmic Sperm Injection (ICSI)

In an alternative procedure (used, for example, for overcoming human male factor subfertility), ICSI was performed. Oocytes were prepared for ICSI by exposure to hyaluronidase solution for 30 seconds (80 IU/mL; Cat No. 10110010, Medi-Cult A/S, Lersø Parkalle 42, 2100 Copenhagen, Denmark) and then transferred into equilibrated Medi-Cult™ or substantially protein-free media of the invention. Human oocytes were incubated for 5-7 minutes in the culture medium under gaseous phase of 5% $CO_2$ in air at 37° C. and then denuded with a denuding pipette (ART No. 1670, International Medical Products BV, Zutphen, Holland). The denuded human oocytes were washed and finally incubated in culture medium for a further 30-60 minutes.

Commercially available ICSI pipettes were used for micromanipulation (Injection Needles, Cat No. 130340B; Holding pipette, Cat No. 13030013; Laboratoire CCD, 60 Rue Pierre Charron, 75008 Paris, France or Injection needle, Cat. No. 10-MIC; holding pipette, Cat. No. 10-MPH-120; Humagen, Charlottesville, Va. 22911, USA). A 5 µL ultra micro-droplet of PVP (Cat No. 1089001, Medi-Cult A/S, Denmark) was thinly spread at the centre of a petri dish (Cat No. 1006, Falcon Plastics, Becton Dickinson, Rutherford, N.J., 07070, USA). The PVP spread was surrounded by up to a maximum of five 10 µL micro-droplets of HEPES-buffered IVF medium (Gamete-1009 Scandinavian IVF Sciences AB, Gothenberg, Sweden). The micro-droplets were overlaid with equilibrated and embryo tested mineral oil (M8410, Sigma Chemicals, USA). Sperm preparation (1 to 2 µL) was introduced at the centre of the PVP spread. ICSI of mature oocytes were performed conventionally (for example, as set forth in Palermo et al., 1992).

Ultra Micro-Droplet Culture

Ultra micro-droplets (UMD; 1.5 to 2 µL for culture of 3 to 7 human embryos) of culture medium were made in 4-well dishes previously filled with equilibrated mineral oil. The dishes were incubated under a gaseous phase of 5% $CO_2$ in air at 37° C. Medium was changed daily (UMD technique) with a finely drawn out Pasteur pipette using equilibrated culture medium in preliminary experiments but not changed (cUMD; or continuous UMD) until day 3 of culture in latter experiments.

Determination of Fertilization

Fertilization was determined 18 h to 20 h after ICSI or IVF. The oocytes were considered fertilized when two distinct pronuclei were visible. Fertilized oocytes were cultured in micro-droplets or ultra micro-droplets of equilibrated medium in an atmosphere of 5% $CO_2$ in air at 37° C. Cleavage and embryo quality were assessed after 24 h.

Zygote Arrest Rate

This parameter was utilized to determine whether the culture medium according to the present inventions causes developmental blocks at the 1-cell stage. The efficacy of the medium can be determined using this assay. Higher proportion of developmental blocks at the 1-cell stage will suggest the medium to be deficient or less efficacious.

Determination of Day 2 Cleaved Embryo Quality

Two parameters were employed to determine the embryo quality of day 2 embryos, viz.: the average blastomere score and the average embryo grade. These were determined as follows:

$$\text{Average blastomere score} = \frac{\text{Total number of blastomeres}}{\text{Total number of embryos}} \quad (i)$$

$$\text{Average embryo grade} = \frac{\text{Total of embryo grades}}{\text{Total number of embryos}} \quad (ii)$$

Since most healthy day 2 human embryos generally attain the 4-cell stage, an average blastomere score 4 and above (in a range of 2 to 6) was considered excellent. The embryos were graded according to a scale of 1 to 4, where the numerical 1 denoted poor quality, and 4, excellent quality. Embryos were graded collectively by a minimum of three (but preferably four) laboratory personnel. In addition, two other parameters included to establish differences in the rate of development of cleavage stage embryos. These were: (i) the proportion of embryos at or above 4-cell stage and (ii) the proportion of embryos that were grade 3 and above, on day 2 of culture in human studies.

Media Formulation

The formulation of an exemplary substantially protein-free media of the invention described herein was as follows. Albumin is known to be a source of fixed nitrogen and nutrients, an antioxidant, and to also have a number of other roles including membrane stabilization. Thus, the substantially protein-free media of the invention substituted albumin with other media components that perform, individually or collectively, the functions of albumin in culture. Individual embryo culture medium components used for these purposes include amino acids (including but not limited to alanine, asparagine, aspartate, cystine, glutamate, glutamine, glycine, histidine, isoluecine, leucine, lysine, methionine, phenylalanine, taurine, thereonine, tryptophan, tyrosine, valine, serine), antioxidants and chelators (for example, EDTA, reduced glutathione, tocopherol), alternate energy sources (such as fructose, glutamine, sodium pyruvate), osmolytes (including mannitol ands myoinositol), vitamins (ascorbic acid, cyanocobalamin, folic acid, tocopherol, etc) and elemental iron.

The concentration of individual components that supported the highest blastocyst development was considered optimal. Three media were formulated (ART-1, ART-2 and ART-3) in the development of the present invention. The inventor has previously described the various experiments undertaken to formulate the substantially protein-free media the ART-7 and ART-7b series from the culture medium ART-1 (Ali, 1997; Ali et al., 2000). The present invention, the PFM-11 protein-free media series were formulated from the culture medium ART-3 (Ali, 1997; Ali et al., 2000).

The final formulations for the various media products of the PFM-11 series are given in tables as set forth below. The concentrations of HEPES and bicarbonate in these media preparations vary, as set forth herein.

The substantially protein-free media of the invention comprise mineral salts, amino acids, antioxidants, antibiotics, energy components and buffer components (HEPES and bicarbonate for incubation under $CO_2$-supplemented conditions) that are similar to but distinct in their particulars from commercially-available, protein-containing media. The substantially protein-free media of the invention uniquely comprise a macromolecular species (methylcellulose and related polymers) and an optionally an un-metabolized sugar alcohol (D-mannitol).

The macromolecule comprising the substantially protein-free media of the invention is methyl cellulose of Formula I:

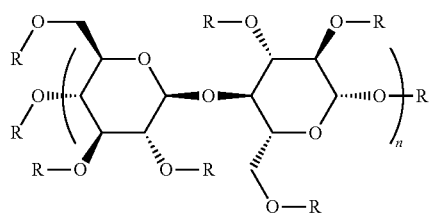

wherein
each R is independently $CH_3$ or H and n is between about 34 and about 43.

In the formula of methylcellulose above, R can be either H or $CH_3$. The extent of methoxy substitution ranges between 27.5-31.5% by weight. Degree of substitution (D.S., average number of substituent groups attached to the ring hydroxyls) is 1.5-1.9. This range gives maximum water solubility. Lower methoxy substitution results in higher solubility in water and is preferred. The code "n" designates the level of polymerization, and optimally corresponds to a molecular weight of 14,000 Daltons relating to an approximate viscosity index of 15 cPS for a 2% solution in water at 20° C. (methylcellulose having these specifications is commercially available from Sigma Chemical Co., St. Louis, Mo. USA; www.sigmaaldrich.com); this corresponds to a value of "n" that is between about 34 and about 43, preferably 36 to 39. The range of this component in the PFM is 0.01 to 0.15 g/L and the most preferred range is 0.09 to 0.1 g/L. The optimal concentration is 0.1 g/L.

Methylcellulose can act as an antioxidant and osmolyte, it is non-toxic, enzyme resistant and not cell permeable (Stewart et al., 1995). It helps to protect gametes and embryos against environmental insults, in particular attack by free radicals and osmotic pressure changes. It protects the cellular membrane from damage and helps maintain homeostasis. It is also a surfactant and lubricant. It contributes to increased viscosity of the medium, so that the gametes and embryos do not stick to sides of dishes and inside pipettes and catheters. These physical attributes are supplied in the absence of serum proteins that normally perform these functions. This substance is inert and safe for human application.

Methylcellulose has been used elsewhere in human pharmaceutical and food industry for well over 25 years without any side effects in human or animal studies. FAO/WHO and EU directives allow consumption of methylcellulose, and it has been used as a negative control in cancer research as it is known to be non-carcinogenic.

Methylcellulose is also used as a thickener and emulsifier in various food and cosmetic products, and has medicinal uses, such as for treatment of constipation. It is not digestible, non-toxic, and not allergenic. Its pharmacological/clinical uses are as excipients and a carrier material. It is used in eye drops, as a bulking agent and laxative, used for diarrhea in functional bowel disease, to control ileostomy output and as absorbent of toxic substances that causes infective diarrhea. It is also an antioxidant.

The substantially protein-free media of the invention also comprises D-mannitol. This compound is poorly absorbed and is excreted almost unchanged in urine. As an antioxidant and an osmolyte this substance can protect the embryo from harmful environmental effects. It thus can further substitute for serum proteins, in part, to protect the embryos against adverse conditions. It is of interest to note that D-mannitol exerts a positive effect on mouse blastocyst development in vitro even in the presence of protein in the media.

In the exemplary substantially protein-free media of this invention (PFM-11), D-mannitol is present at a preferred concentration of 2.8 micromolar (the most preferred concentration) within the range of 0.056 to 6.9 micromolar. The more preferred range is 1.4 to 5.5 micromolar; even more preferred within the range of 2.5 to 3.0 micromolar. The most preferred concentration is about 2.7 micromolar. The empirical formula of D-mannitol is $C_6H_{14}O_6$ and has the structural formula:

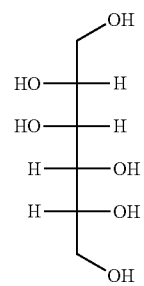

D-mannitol is a food additive, used in cakes, confectionaries and sweets; being sweeter than sucrose, it is considered an alternative sweetener for diabetics. It is an osmolyte and antioxidant. It has been used in high concentrations to treat acute stroke for well over 30 years. Hypermolar concentrations of this compound are used to treat severe brain damage and elevated intracranial pressure. It is a diuretic and is used for dieresis in instances of poisoning, or to measure extracellular fluid compartment. It also has laxative effects in mammals including man. No adverse effects in man have been reported as a result of clinical application of D-mannitol as a therapeutic agent. It is also non-cytotoxic and non-mutagenic in several species. D-mannitol is poorly absorbed and is excreted (Milde, 1965; Widdowson and Dickerson, 1965). The inclusion of this substance in culture medium increased blastocyst development in the mouse even in the presence of serum proteins, suggesting a positive role in embryo culture as an antioxidant and osmolyte (Ali, unpublished observations). Its use is permitted by the FDA and the EU, and FAO/WHO has concluded it to be safe for human consumption.

In the solutions and formulations of the invention, D-mannitol of Formula II is present at a concentration of from about 0.05 micromolar to about 6.9 micromolar. The more preferred range is 1.4 to 5.5 micromolar. The most preferred concentration is about 2.8 micromolar.

The skilled worker will appreciate that the role of serum proteins are numerous, and in its absence, one or two components by themselves may not provide a complete substitute for proteins in the medium. Thus, the skilled worker will recognize that the invention does not merely provide media supplemented with methylcellulose and D-mannitol. Rather, the invention provides media comprising in addition a complex mixture of additional components, preferably in optimal concentrations, and the selective exclusion of commonly used media components that have proven detrimental to embryos in culture. Some of these include:

(i) Including unique concentrations for two amino acids (L-taurine and glutamine) that are the principal providers of nutrition and osmotic balance. These amino acids are provided at concentrations within the range of 1 mM to 30 mM L-taurine and 1 mM to 50 mM L-glutamine, more preferably 10 mM to 30 mM L-taurine and 10 mM to 30 mM L-glutamine and most preferably 20 mM each of L-taurine and L-glutamine.

(ii) Including as energy sources any one or plurality of compounds (including D-glucose, fructose, or pyruvate) that are less likely to cause developmental blocks in human embryos. Optimal concentrations of fructose are from about 0.5 mM to 6.0 mM fructose, with a more preferred concentration being from about 1 mM to 5.6 mM, and a most preferred concentration of about 5.1 mM. The optimal concentrations of the remaining two energy sources are given elsewhere in this document.

(iii) Including the following concentrations of certain amino acids.

| Name | Optimum range Conc. in PFM (mM) | Preferred range (mM) | Most preferred Conc. (mM) |
|---|---|---|---|
| L-alanine | 0.1-10 | 0.45-0.55 | 0.5 |
| L-arginine | 0.018-0.18 | 0.072-0.125 | 0.072 |
| L-cystine•2HCl | 0.0025-0.025 | 0.01-0.02 | 0.01 |
| L-glutamate | 0.01-1.0 | 0.45-0.55 | 0.5 |
| L-glycine | 0.1-1.0 | 0.2-0.3 | 0.25 |
| L-histidineHCl•H$_2$O | 0.005-0.05 | 0.02-0.04 | 0.02 |
| L-isoleucine | 0.01-0.1 | 0.04-0.08 | 0.04 |
| L-leucine | 0.01-0.1 | 0.04-0.08 | 0.04 |
| L-lysine HCl | 0.0125-0.125 | 0.05-0.1 | 0.05 |
| L-methionine | 0.0025-0.025 | 0.01-0.02 | 0.01 |
| L-phenylalanine | 0.005-0.05 | 0.02-0.04 | 0.02 |
| L-threonine | 0.01-0.1 | 0.04-0.08 | 0.04 |
| L-tryptophan | 0.00125-0.0125 | 0.005-0.01 | 0.005 |
| L-tyrosine•2Na2H2O | 0.005-0.05 | 0.02-0.04 | 0.02 |
| L-valine | 0.01-0.1 | 0.04-0.08 | 0.04 |

(iv) Including the following concentrations of water soluble vitamins.

| Name | Optimum range (mM) | Preferred range Conc. (mM) | Most preferred Conc. (mM) |
|---|---|---|---|
| Choline chloride | 0.004-0.007 | 0.004-0.005 | 0.004 |
| D-Biotin | 0.0024-0.004 | 0.0024-0.003 | 0.0024 |
| Folic acid | 0.0014-0.0023 | 0.0014-0.0016 | 0.0014 |
| Myoinositol | 0.0067-0.011 | 0.0067-0.0078 | 0.0067 |
| Niacinamide | 0.005-0.008 | 0.005-0.0057 | 0.005 |
| D-pantothenic Acid•½Ca | 0.0025-0.004 | 0.0025-0.003 | 0.0025 |
| Pyridoxine HCl | 0.003-0.005 | 0.003-0.0034 | 0.003 |
| Riboflavin | 0.00016-0.00027 | 0.00016-0.00019 | 0.00016 |
| Thiamine HCl | 0.0018-0.003 | 0.0018-0.002 | 0.0018 |

The range for vitamin B12 is as follows:

| Name | Optimum range Conc. in PFM (pM) | Preferred range (pM) | Most preferred Conc. (pM) |
|---|---|---|---|
| Vitamin B12 | 443-885 | 590-738 | 616 |

(v) Including vitamin L (Vitamin E Type 6, Sigma Chemical Co.) at a concentration of from 5 micromolar to 20 micromolar, more preferably 8 micromolar to 12 micromolar, even more preferably 10 micromolar.

(vi) Excluding L-asparagine, L-aspartate and L-serine that can be detrimental to the development of zygotes and early cleavage stage embryos.

(vii) Excluding elemental iron, that can be detrimental to embryo development.

(viii) Including reduced glutathione (GSH) at a concentration of 60 micromolar to 500 micromolar, and more preferably 250 micromolar to 350 micromolar, and even more preferably 300 micromolar.

Other Compounds
Concentration in Final Solution

| Description | Range | Preferred Range | Most Preferred Conc. |
|---|---|---|---|
| D-glucose | 0.75-1.0 | 0.75-0.90 | 0.78 g/L |
| Sodium chloride | 6.12-6.95 | 6.12-6.19 | 6.171 g/L |
| Potassium chloride | 0.35-0.4 | 0.35-0.36 | 0.355 g/L |
| Calcium chloride - | 0.23-0.27 | 0.23-0.24 | 0.235 g/L |
| Magnesium sulfate | 0.086-0.098 | 0.086-0.087 | 0.087 g/L |
| Sodium dihydrogen phosphate | 0.107-0.122 | 0.107-0.109 | 0.108 g/L |
| EDTA, Sodium | 0.0416-0.043 | 0.0416-0.042 | 0.0418 g/L |
| Sodium bicarbonate* | 2.2 | 2.2 | 2.2 g/L |

| | -continued | | |
|---|---|---|---|
| Sodium lactate, 60% syrup | 1.9 | 1.9 | 1.9 ml/L |
| Phenol red | 0.011 | 0.011 | 0.011 g/L |
| *Sodium bicarbonate | | | |
| In Fertilization and Culture media | 2.2 g/L (26.2 mM) | 2.2 g/L (26.2 mM) | 2.2 g/L (26.2 mM) |
| In Gamete Handling Media | 2.2 g/L (26.2 mM) | 2.2 g/L (26.2 mM) | 2.2 g/L (26.2 mM) |
| In Flushing medium | 2.2 g/L (26.2 mM) | 2.2 g/L (26.2 mM) | 2.2 g/L (26.2 mM) |
| **HEPES | | | |
| In Fertilization and Embryo Culture media | | 0 mM | |
| In Gamete Handling Media | | 15 mM | |
| In Flushing medium | | 25 mM | |

The PFM-11 media series set forth herein differs from conventional embryo culture media in at least the following aspects:

1. Absence of adding donor serum proteins to media—this eliminates the potential for disease transmission, making the PFM-11 media series according to the present invention non-hazardous.
2. The presence of methylcellulose and D-mannitol.
3. Alterations in the composition of the media regarding species and concentrations of amino acids, antioxidants, vitamins, energy sources and mineral salts, all optimized for embryo culture.

Among the advantages of the media of the invention are reduced risks to patients/healthcare workers. The substantially protein-free media of the invention is also advantageous because it reduces risks to patients, their babies and healthcare workers exposed to the media. While certain risks remain these are minor in comparison with the infectious risks avoided using the substantially protein-free media of the invention. These risks include allergies to the components used. The chance of this occurring is very unlikely because the ingredients except for antibiotics are mostly inert and non-reactive. All ingredients are in minute concentrations not likely to elicit an allergic response.

Clinical Trial

A clinical trial was approved for the transfer of embryos generated in the final formulations of the PFM-11 media series. The clinical trial also investigated the difference in efficacy of the PFM-11 media series when fertilization was performed either by conventional IVF and ICSI.

Statistical Analysis

Statistical comparisons were performed with the 2-sample t-test or two by two tables. A value of $p<0.05$ or less was considered statistically significant.

RESULTS

Culture Characteristics of Sibling Human Oocytes when Inseminated by Conventional IVF in PFM-11 Protein-Free Medium and MediCult™ Embryo Culture Media The fertilization rate of sibling oocytes after conventional IVF was similar in the control MediCult™ and the PFM-11 media (Table A). A higher proportion of zygotes arrested in the control MediCult™ medium (8.1%) compared to (2.2%) the PFM but this was not statistically significant. The quality of cleaved day 2 human cIVF sibling embryos generated in the PFM-11 in ultramicroplet culture was significantly superior in terms of blastomere number and grade compared to those generated in the control medium. In the PFM-11 medium the average blastomere number was 3.4 and the average embryo grade was 3.1 (n=116). In the control medium (MediCult™) the average blastomere number was similar (p=0.865) at 3.4 and the average embryo grade was significantly lower (p=0.001) at 2.7 (n=118). The proportion of embryos that had attained the $\geq$4-stage was similar in both groups but the proportion of embryos that were above grade $\geq$3 was significantly higher the PFM-11 protein-free group.

TABLE A

Quality of day 2 human sibling embryos generated by conv. IVF in protein-free PFM-11 medium

| Medium | Fertil % | Arrested @ 1-cell stage % | Blast number Mean (1 SD) | Grade Mean (1 SD) | % ≥4 cells | % ≥3 Grade |
|---|---|---|---|---|---|---|
| PFM-11 (−protein) | 85.3 (116/136) | 2.2 | 3.4 (1.0) | 3.1 (0.9) | 58.4 | 74.3 |
| MediCult™ (+protein) | 79.2 (118/149) | 8.1 | 3.4 (1.0) | 2.7 (0.8) | 56.2 | 58.1 |
| Significance | p = 0.235 | p = 0.052 | p = 0.865 | p = 0.001 | p = 0.847 | p = 0.017 |

[Embryo grade: 4 = excellent; 3 = good; 2 = fair; 1 = poor];
Control embryos generated by ICSI or IVF;
Blast = blastomere;
Findings: Test medium superior to control Culture Characteristics of Sibling Human Oocytes when Inseminated by Conventional IVF in PFM-11 Protein-Free Medium and MediCult™ Embryo Culture Media The fertilization rate of sibling oocytes after ICSI was statistically higher in the protein-free PFM-11 medium compared to the control MediCult™ (77.8% vs 69.4%, p=0.043; Table B). The developmental arrest at the zygote stage was lower in the PFM-11 medium compared to the MediCult™ medium but this difference was not statistically significant (2.8 vs 6.3% respectively, p=0.088). The quality of cleaved day 2 human ICSI sibling embryos generated in the PFM-11 medium cultured in ultra micro-droplets was significantly superior in terms of blastomere score compared to those generated in the control medium (3.8 vs 3.3 respectively, p=0.001). The average embryo grade of embryos generated in the PFM-11 medium was similar to that of embryos generated in the control medium (2.9 vs 2.8, p=0.080). The proportion of embryos that had attained the ≧4-stage was similar in both groups but the proportion of embryos that were above grade ≧3 was significantly higher the PFM-11 protein-free group.

TABLE B

Quality of day 2 human sibling embryos generated by ICSI in protein free PFM-11 medium

| Medium | Fertil % | Arrested @ 1-cell stage % | Blast number Mean (1 SD) | Grade Mean (1 SD) | % ≧4 cells | % ≧3 Grade |
|---|---|---|---|---|---|---|
| PFM-11 (−protein) | 77.8 (196/252) | 2.8 | 3.8 (1.2) | 2.9 (0.7) | 71.4 | 63.5 |
| MediCult ™ (+protein) | 69.4 (175/252) | 6.3 | 3.3 (1.1) | 2.8 (0.8) | 54.8 | 58.6 |
| Significance | p = 0.043 | p = 0.088 | p = 0.001 | p = 0.080 | p = 0.002 | p = 0.413 |

(Embryo grade: 4 = excellent; 3 = good; 2 = fair; 1 = poor);
Blast = blastomere;
Control embryos generated by ICSI/IVF;
Findings: test medium superior to control Clinical Trial The conventional IVF clinical pregnancy rate with substantially protein-free PFM-11 media is increased to 50. % (14 of 28) in all age groups and up to 53.8% (14 of 26) in women below 40 years of age; when compared to currently available embryo media containing proteins (33% pregnancies for all age groups combined; cited from Ali, 2004). The ICSI clinical pregnancy rate with substantially protein-free PFM-11 media is likewise increased to 46.2% (12 of 26) in all age groups and up to 54.5% (12 of 22) in women below 40 years of age. This difference is statistically significant in favor of the present substantially protein-free PFM-11 media, indicating that the substantially protein-free media of this invention is at least equivalent to (and can be superior to) currently-available commercial protein-containing medium currently available in the market. The number of babies born from embryos generated in the PFM-11 media by conventional IVF was 12 babies (30.8%, that is 8 of 26 women treated delivered; or 61.5% 8 of 13 of the pregnant women delivered; one pregnancy lost to follow-up) and by ICSI, also 12 babies (36%, that is 8 of 22 women treated delivered or 66.7% (8 of 12) or of the pregnant women delivered. The babies born from embryos generated in the PFM-11 of the invention are apparently normal, intelligent, talkative and active (according to parental reports). These statistical data were produced from a sample of at least 24 children from such births.

Significance of Results

The availability of a chemically defined medium for generating viable early cleavage stage human embryos improves the safety of patients undergoing assisted reproduction treatment (ART) because, inter alia, potentially hazardous donor protein can be eliminated from the media. This is a particular concern with regard to transmission of pathogenic diseases, in particular viral diseases, such as human acquired immunodeficiency disease syndrome (AIDS) and hepatitis, or Creutzfeldt-Jakob disease (CJD) transmitted by prions, or others in blood-derived products has led a number of embryologists worldwide to seek (unsuccessfully) alternative(s) to donor protein for their embryo culture and handling procedures. The danger is certainly real: in the past an epidemic of hepatitis B occurred in about 200 IVF patients that received embryos cultured in medium containing pooled sera contaminated with hepatitis B virus (van Os et al., 1991). More recently the scientific community was confronted with the dilemma of having to inform their patients that a commercial preparation of a culture medium used for embryo culture and handling may be contaminated with albumin donated by a person who later died of CJD (Kemmann, 1998).

In addition to pathogens and prions, serum or proteins derived from serum such as albumin may contain embryotoxic factors, as in patients with endometriosis, recurrent abortion and those suffering from unexplained infertility (Miller et al., 1995). These embryotoxic factors, the nature of which remains to be elucidated, have been shown to be detrimental to embryos in vitro (Miller et al., 1995; Fein et al., 1995). Moreover, the use of serum or albumin raises the problem of reproducibility, because batch-to-batch variation in sera or albumin has been well recognized. An inability to control quality of different batches of sera can affect quality of embryos generated. Problems associated with embryotoxicity and/or non-reproducibility of the quality of serum proteins are avoided, of course, when chemically defined medium is used instead of culture media containing donor proteins.

The quality of embryos generated in the PFM-11 culture medium under ultra microdroplet culture conditions was similar to or somewhat better than those generated in the control medium containing proteins when performed under similar culture conditions. More importantly the fertilization rate, the zygote arrest rate and the quality of embryos generated in the novel substantially protein-free medium PFM-11 medium is not inferior to that observed in the control medium containing proteins for any of the parameters tested. On the other hand the control medium has proven inferior in some of the parameter tested. The clinical trial showed that the PFM-11 medium is as efficacious or better than the control embryo culture medium containing proteins for day 2 embryos. Moreover it is completely safe as it is devoid of hazardous donor proteins of biological origin.

Improved quality of embryos generated in micro-droplets have been earlier shown to be due to autocrine and paracrine effects of certain growth factors released by the embryo into the medium (Paria and Dey, 1990; Paria et al., 1991; Canesco et al, 1992). Indeed, the addition of hIGF-1 to culture medium was found to enhance human pre-implantation development, in particular, blastocyst formation was significantly improved (Lighten et al., 1998). Recently communal culture of human embryos was reported to result in higher implantation and pregnancy rate in human assisted reproduction (Almagor et al., 1996). The effect of growth factors in pre-implantation development has been extensively reviewed by Kane et al. (1997). Evidence from previous studies on the effect of growth factors indicates a lack of clear growth pattern on embryo development in vitro. Autocrine growth factors may be essential for embryo development under stressful culture conditions. Growth factors that may show positive effects on embryo pre-implantation development include CSF-1; IGF-I; IGF-II; TGF-α, and possibly LIF.

Fertilization in human oocytes was found to occur in PFM-111 with spermatozoa prepared in a PFM-11. Capacitation was not affected. PFM-111 has been shown herein to be efficacious in promoting fertilization in the absence of serum proteins in the medium. The high fertilization rate during conventional IVF using PFM-11 indicated that the absence of protein in the medium did not impair sperm capacitation, fertilization, and embryo development in vitro and subsequent viability in utero. In spite of a deficiency of proteins in the medium, sperm capacitation, penetration of sperm into the oocyte and fertilization occurred.

The clinical pregnancy, delivery and abortion rates were significantly better in the test group (using substantially protein-free media of the invention) compared to the control (using conventional protein-containing media). Also, the proportion of pregnant women in the test group that delivered was similar to the world average reported for cleavage stage embryo transfers (DeMouzon and Lancaster, 1997).

The results of the experiments disclosed herein revealed that: (i) penetration of spermatozoa into oocytes during conventional IVF, gamete interaction and subsequent fertilization in the human following both conventional IVF or ICSI were not impaired using substantially protein-free media PFM-11 of the invention, (ii) the resultant early cleavage stage embryos were viable and capable of eliciting clinical pregnancies, (iii) the quality of early cleavage stage embryos generated in the PFM-11 was in general similar or somewhat superior to that generated in control medium containing serum proteins.

Stringent purification and sterilization measures employed for preparations of animal origin cannot exclude with absolute certainty the possibility of transmission of unknown pathogens (Truyen et al., 1995). With the formulation of substantially protein-free media and the substitution of hyaluronidase with a recombinant hyaluronidase such as Cumulase®, it is now possible to perform the entire laboratory assisted reproduction procedures with no apparent risk of transmission of disease to IVF patients.

In conclusion, the substantially protein-free PFM-11 medium of the present invention was demonstrated to be efficacious, with sperm penetration into oocyte during conventional IVF, and fertilization following ICSI or conventional IVF, being uncompromised. Pregnancies were also not compromised when embryos generated in the PFM were transferred, with a clinical pregnancy rate of above 50% in women 39 years and below. Overall the PFM-11 medium was equally efficacious if not superior to medium containing serum proteins in the generation of viable human embryos. The routine use of PFM in human assisted conception procedures can eliminate the potential risk of transmission of diseases through protein-bound pathogens or dangerous prions. This study showed that it is possible to generate viable human embryos in a medium devoid of added protein in a cell-free culture system.

PREPARATION OF PFM-11 OF THE INVENTION

Basal Salt Solution (BSS) Stock Solution 1:

Preparation of stock solution of basal salts (Basal Salt Solution—BSS) to be used is a final formulation of PFM Culture medium, Gamete handling medium and Flushing medium.

|   | Raw material component | Quantity (g/L) |
|---|---|---|
| 1. | Calcium chloride•2 $H_2O$ | 2.65 (23.8 mM) |
| 2. | Magnesium sulphate (anhyd.) | 0.9767 (8.1 mM) |
| 3. | Potassium chloride | 4.0 (53.7 mM) |
| 4. | Sodium chloride | 69.53 (1.2 M) |
| 5. | Sodium phosphate monobasic (anhyd.) | 1.22 (10 mM) |
| 6. | D-glucose | 10.517 (58.4 mM) |
| 7. | Phenol red | 0.11 (0.31 mM) |
| 8. | WFI (Water for injection) | 950 mL |

Preparation procedure:

1. Rinse mixing container with WFI (Water for injection, 18.2 MegaOhms resistivity) before preparation of stock solution.
2. Add component 1 to 1000 mL of WFI water as it is extremely hydroscopic.
3. Add components 2-7 in order, mixing continually and make up final volume to 1000 mL using WFI.
4. Sterile filtration to be carried out immediately after all solutes are fully dissolved. Do not filter if solutes remain. 0.1 micron filters can be used but avoid excessive pressure when filtering. The Stock 1 solution can be pre-filtered with 0.2 micron filter followed by 0.1 micron filter.
5. There should be no precipitate or cloudiness post-filtration.
6. Fill into containers of suitable volume, e.g. bottles.
7. Cap bottles (preferably tamper-evident seal bottles).
8. Store in the dark between 2 and 6 degrees Celsius.

Storage and Shelf Life.

The Basal Salt Solution (BSS) stock was stable for two months when stored between 2 and 6 degrees Celsius. Always check stored BSS stock carefully for precipitates or cloudiness before use. Discard if precipitates occur or the solution has turned cloudy during storage.

Inclusion Volumes of BSS Stock 1 in Final Product:

Where sodium bicarbonate is the predominantly active buffer component in the formulation (Culture media products), 70 ml** of BSS must be present in every 1000 ml of final formulation prepared.

Where HEPES is the predominantly active buffer component in the formulation (sperm/flushing media products), 50 mL of BSS is added for every 1000 mL of final formulation prepared.

Adjusting the Osmolality of Final Medium with BSS or WFI Water to Increase or Decrease (Respectively) the Osmolality of the Medium:

Should the osmolality of the final medium be 285 mOsmols when final volume is less than 1000 ml (i.e. after adding BSS, BAAS and BVS); then separately dilute a small amount of BSS with WFI. Use 1 volume of BSS with 9 volumes of WFI water to give a working BSS (WBSS). Adjust osmolality of WBSS to 285 mOsmols. Make up final volume of final medium to 1000 ml with adjusted WBSS.

For composition of final formulation from all stock solutions—see Stock 4 instructions.

Basal Amino Acid Solution (BAAS) Stock Solution2:

This protocol was used to prepare a 1 litre stock solution of basal amino acids in solution (Basal 5 Amino Acid Solution—BAAS) for inclusion in final formulations of PFM Culture medium, Gamete Handling medium and Flushing medium.

Reagents

| | Raw material component | Quantity (g/L) | |
|---|---|---|---|
| 1. | L-arginine HCl | 1.26 | (6.0 mM) |
| 2. | L-cystine (L cystine•2HCl)* | 0.313 | (1.0 mM) |
| 3. | L-histidine HCl•H2O | 0.42 | (2.0 mM) |
| 4. | L-isoleucine | 0.52 | (4.0 mM) |
| 5. | L-leucine | 0.52 | (4.0 mM) |
| 6. | L-lysine•HCl | 0.752 | (4.1 mM) |
| 7. | L-methionine | 0.15 | (1.0 mM) |
| 8. | L-phenylalanine | 0.32 | (1.9 mM) |
| 9. | L-threonine | 0.48 | (4.0 mM) |
| 10. | L-tryptophan | 0.1 | (0.49 mM) |
| 11. | L-tyrosine (L-tyrosine•2Na 2H$_2$O)* | 0.519 | (2.0 mM) |
| 12. | L-valine | 0.46 | (3.9 mM) |
| 13. | WFI (Water for injection) | 1000 mL | |

Instructions for Preparation of Stock 2 BAAS
1. Rinse mixing containers with WFI (Water for injection, 18.2 MegaOhms resistivity)
2. Dissolve components 1, 2 and 4-11 in 400 mLs of WFI.

Compliance with Supplier's storage recommendations is required as difficulties with solubility may be experienced with less than optimal conditions. If a precipitate occurs discard and start again using 25 mL of 0.11 N NaOH and 275 mL of WFI. Sodium hydroxide is only used as last option.
3. L-histidine HCl—H$_2$O and L-valine can be difficult to dissolve and in such circumstances solubility can be achieved by using 1N HCl. Components 3 and 12 should be dissolved in their own separate 300 mL volumes of WFI. Use only the smallest volume possible of 1N HCl to achieve solubilization. The maximum amount of 1N HCl (embryo tested) that should be used is 25 mL in 300 mL of WFI. Avoid heating water, alkalis and acids above 37 degrees Celsius to dissolve all components.
4. Once components 3 and 12 are fully dissolved, make up final volume of 1000 mL by gradually adding in a stepwise manner, a 200 mL portion of the water soluble amino acids made in step 2 to:
(a) 300 mL solution of L-histidine HCl.H$_2$O giving 500 mL in total volume.
(b) 300 mL solution of L-valine giving 500 mL in total volume.
5. Combine both 500 mL volumes, gradually in a stepwise manner with constant mixing to avoid precipitation.
6. Sterile filter solution with 0.2 micron filter immediately.
7. Fill into containers of suitable volume (e.g. bottles).
8. Cap bottles (preferably tamper-evident seal bottles).
9. Store in the dark between 2-6 degrees Celsius.
Storage and Shelf Life.

The Basal Amino Acid Solution (BAAS) stock will keep for two months when stored between 2 and 6 degrees Celsius. Always check stored BAAS stock carefully for precipitates or cloudiness before use. Discard if precipitates or cloudiness occurs during storage.
Inclusion Volumes of BAA Stock in Final Product:

10 ml of BAA stock solution should be used per 1000 ml in the preparation of all final formulations.

L-Tyrosine.2Na 2H$_2$O and L-Cystine.2HCl were used because free form L-Tyrosine and L-Cystine were not commercially available.
Basal Vitamin Solution (BVS) Stock Solution 3.

The protocol according to this example prepares a 1 litre stock solution of basal vitamins in solution (Basal Vitamin Solution—BVS) for inclusion in final formulations of PFM Culture medium, Gamete handling medium and Flushing medium.
Reagents

| | Raw material component | Quantity (g/L) | |
|---|---|---|---|
| 1. | Choline chloride | 0.1 | (0.7 mM) |
| 2. | D-biotin | 0.1 | (0.4 mM) |
| 3. | Myoinositol | 0.2 | (1.1 mM) |
| 4. | Niacinamide | 0.1 | (0.82 mM) |
| 5. | D-pantothenic acid | 0.1 | (0.46 mM) |
| 6. | Pyridoxine HCl | 0.1 | (0.49 mM) |
| 7. | Riboflavin | 0.01 | (26.5 µM) |
| 8. | Thiamine HCl | 0.1 | (0.33 mM) |
| 9. | Folic acid | 0.1 | (0.23 mM) |
| 10. | WFI (Water for injection) | 1000 mL | |

Instructions for Preparation of Stock 3 (BVS)
1. Dissolve components 1-7 in 800 mL of WFI water (Water for injection, 18.2 MegaOhms resistivity). Should any component not dissolve, small amounts of 0.1 N or 1 N NaOH can be used to achieve solvation as a last option.
2. Dissolve component 8 in 2.5 mL of 0.1 N NaOH and add carefully in a stepwise manner, with constant mixing to 800 mL containing components 1-7.
3. Make up volume to 1000 mL using WFI water with constant mixing and sterile filter immediately with 0.2 micron filter into suitable containers (e.g. 60 mL Nalgene bottles, tamper-evident bottles).
4. Cap bottles.
5. Store in the dark at −20 degrees Celsius.
Storage and Shelf-Life.

The Basal Vitamin Solution (BVS) stock can be stored for two months when stored at −20 degrees Celsius in 60 mL aliquots. Always check thawed BVS stock 3 carefully for precipitates or cloudiness before use. Discard if precipitates appear or the thaw solution appears cloudy.

Inclusion volumes of BVS stock into final product:

6.0 mL of BVS stock solution should be used per 1000 mL in the preparation of all final formulations prepared—see Stock 4.
Stock 4 Solution and Final Formulation Combinations.

The preparation of Stock 4 permits the final addition of the unique chemicals in this Formulation and the addition of specific volumes taken from Stock 1 Basal Salts Solution (BSS), Stock 2 Basal Amino Acid Solution (BAAS) and Stock 3 Basal Vitamin Solution (BVS). The protocol describes the addition of buffers and antibiotics that are specific to the media formulation being prepared, i.e. Culture Gamete handling and Flush media.

The following protocol prepares 1 litre of final formulation of Culture medium, Gamete handling or Flush medium. Larger batches may be prepared by appropriate scaling of quantities.

Reagents

|   | Raw material component | Quantity (g/l) |
|---|---|---|
| 1. | Sodium pyruvate | 0.02975 (0.27 mM) |
| 2. | Fructose | 0.92125 (5.1 mM) |
| 3. | Glycine | 0.01875 (0.25 mM) |
| 4. | Glutathione (Reduced) | 0.09225 (0.30 mM) |
| 5. | D-mannitol | 0.0911 (0.5 mM) |
| 6. | EDTA (sodium tetra) | 0.04175 (0.10 mM) |
| 7. | L-alanine | 0.04455 (0.5 mM) |
| 8. | L-taurine | 1.251 (1.0 mM) 20 mM |
| 9. | L-glutamic acid mono sodium | 0.0735 (0.39 mM) |
| 10. | Lactic acid Sodium salt | 1.9 mL per liter |
| 11. | Vitamin B-12 | 100 µL/L |
| 12. | Vitamin E Type 6 | 333 µL/L |
| 13. | Stock 1 BSS | 70 mL |
| 14. | Stock 2 BAAS | 10 mL |
| 15. | Stock 3 BVS | 6 mL |

|   | | Quantity g/L Culture medium | Quantity g/L Gamete handling Medium | Quantity g/L Flush medium |
|---|---|---|---|---|
| 16. | Gentamycin sulphate | 1.5 | 4 (sperm) 1.5 (oocyte) | 1.5 |
| 17. | Penicillin G | 75 | 0 (sperm) 75 (oocyte) | 75 |
| 18. | L-glutamine | 1.461 (20 mM) | 1.461 (20 mM) | 1.461 (20 mM) |
| 19. | Sodium bicarbonate | 2.2 (26.2 mM) | 2.2 (26.2 mM) | 2.2 (26.2 mM) |
| 20. | HEPES | 0.0 | 3.5745 (15 mM) | 5.9575 (25 mM) |
| 21. | Methyl cellulose | 0.1 | 0.1 | 0.1 |
| 22. | WFI (Water for injection) | 1000 mL | 1000 mL | 1000 mL |

Instructions for Preparation of Stock 4 and Final Formulation Combination.
1. Rinse mixing vessel with WFI (Water for injection, 18.2 MegaOhms resistivity).
2. Dissolve components 1-11 in 700 mL of WFI mixing continuously whilst the additions are made.
3. Add components 12-15 and make up to 900 mL with WFI and continue mixing.
4. Add components 16-21 depending on preparation of the basic formulation type i.e. PFM Culture media, PFM Gamete media handling medium and PFM Flush medium.
5. Adjust osmolality of all three media and separately filter sterilize using 0.2 microns pore-size filters, 0.1 micron filter can also be used but avoid using pressure. Do not use 0.1 microns filter if high pressure required for filtering the solution.
6. Sterile filter immediately into final packaging (Nalgene bottles).:
PFM Culture media is filled into 60 mL bottles
PFM Gamete handling media is filled into 60 mL bottles.
PFM Flush medium is filled into 125 mL bottles.
(Bottles used are preferably tamper-evident bottles.)
7. Cap bottles.
8. Label bottles.
9. Store in the dark at between 2 and 6 degrees Celsius.
Footnote for Stock 4 and Final Formulation Combination.
Check osmolality. If the osmolality is high, then adjust to 285 mOsmols by adding WFI pure water. The amount to be added is calculated as follows:

[Osmolality of medium−Desired osmolality (i.e., 285)/Osmolality of medium]×volume of medium Example: If osmolality of medium is 300 and volume of medium is 900 ml as above, then calculate as shown below:

[300−285/300]×900=15/300×900=45

Therefore if you add 45 ml of water to the medium and then measure osmolality again, you should theoretically have an osmolality of about 285 plus/minus 2 or 3 units. Be very careful not to add too much water because the important ingredients in the medium will become diluted and will affect the efficacy of the medium, even if you bring back the osmolality of the medium by adding more Stock 1 BSS solution.

However, if osmolality is lower than 285 mOsmols, add Stock 1 BSS only to the medium, approximately 2 to 3 mOsmols increases per ml of Stock 1 BSS but this may not always be predictable. So be very careful not to add too much. Add a little at a time and measure osmolality.

REFERENCES

Ali J. (1997) Formulation of a protein-free culture system for the culture of human embryos: preliminary findings and pregnancies. In: Programme and abstract book of the 16th Annual Scientific meeting of the Fertility Society of Australia, 2-4 Dec. 1997, Adelaide, Australia, p 34 (Abstract)

Ali J. (2000) Investigation into the nutrient requirement of the human embryos: Successful formulation and clinical trial of a novel protein-free embryo culture medium. Emirates Med J. 18:195-202

Ali, J (2004) Generation of viable human embryos in a protein-free embryo culture (ART-7b) medium enhances clinical pregnancy rate and prevents disease transmission in assisted reproduction. Middle East Fertil Soc. J. 9:118-127

Ali, J., Abdulkader, A., Shahata, M. A. M. et al. (1998) Term deliveries from human embryos conceived in a novel culture medium devoid of added protein. Middle East Fertil. Soc. J. 3, 40 (Abstract)

Ali, J., Whitten, W. K. and Shelton, J. N. (1993). Effect of culture systems on mouse early embryo development. Hum. Reprod. 8, 1110-1114

Almagor, M., Bejar, C., Kafka, I. et al. (1996) Pregnancy rates after communal growth of pre-implantation human embryos in vitro. Fertil. Steril. 66, 394-397

Balakier, H. (1993) Tripronuclear human zygotes: the first cell cycle and subsequent development. Hum. Reprod. 8, 1892-1897

Barber, A. A. (1961) Inhibition of lipid peroxide formation by vertebrate blood serum. Arch. Biochem. Biophys. 92, 38-43

Barnes, R I, Crombie, A., Gardner, D. K. et al. (1995) Blastocyst development and pregnancy after in vitro maturation of human primary oocytes, intracytoplasmic sperm injection and assisted hatching. Hum. Reprod. 10, 3243-3247

Bavister, B. D. (1995) Culture of pre-implantation embryos: facts and artifacts. Hum. Reprod. Update 1, 91-148

Biggers, J. D. Summers, M. C. and McGinnis, K. L. (1997) Polyvinyl alcohol and amino acids as substitutes for bovine serum albumin in culture media for mouse pre-implantation embryos. Hum. Reprod. Update 3, 125-135

Boyers, S. P. Diamond, M. P. Lavy, G. et al. (1987) The effect of polyploidy on embryo cleavage after in vitro fertilization in humans. Fertil. Steril. 48, 624-627

Canesco, R. S. Sparks, A., Pearson, R. E. et al. (1992) Embryo density and medium volume effects on early marine embryo development. J. Assist. Reprod. Genet. 9, 454-457

Caro, C. M. and Trounson, A. (1986) Successful Fertilization, Embryo Development, and Pregnancy in Human in Vitro Fertilization (IVF) Using a Chemically Defined Culture Medium Containing No Protein. Journal of in Vitro Fertilization and Embryo Transfer, vol. 3, no. 4. p. 215-217)

Carrillo, A. J., Lane, 13., Pridham, D. D. et al. (1998) Improved clinical outcomes for in vitro fertilization with delay of embryo transfer from. 48 to 72 hours after oocyte retrieval: use of glucose- and phosphate-free media. Fertil. Steril. 69, 329-334

Centers . for Disease Control. (1985) Fatal degenerative neurologic disease in patients who received pituitary derived human growth hormone. MMWR Morb Moral Wkly Rep 34:359-60, 365-6.

Cholewa, J. A. and Whitten, W. K. (1965) Development of 2-cell mouse embryos in the absence of a fixed nitrogen source. J. Reprod. Fertil. 22, 553-555

Cockle S M, Aitken A, Beg F, Morrell J M, Smyth D G. (1989) The TRH-related peptide by pyroglutamylglutamylprolinamide is present in human semen. FEBS Lett 1989; 252: 13-7

Dandekar, P. V. and Glass, R. H. (1990) Development of two-cell mouse embryos in protein-free and protein-supplemented media. J. In Vitro Fertil. Embryo Transfer 7, 107113

De Mouzon, J. and Lancaster, P. (1997). World collaborative report on in vitro fertilization. Preliminary data for 1995. J. Assist. Reprod. Genet. (suppl.) 14, 250S-265S Drakakis, P., Loutradis, D., Milingos, S. et al. (1996) The in vitro development of mouse embryos beyond the blastocyst stage into the hatching and outgrowth stage using different energy sources. J. Assist. Reprod. Genet. 13, 786-792

Du, Z. F. and Wales, R. G. (1993) Effect of culture from the zygote stage on the metabolism of glucose and glutamine by 2-cell embryos and blastocysts recovered from. outbred or H female mice. Reprod. Fertil. Dev. 5, 555-565

Esmonde T, Lueck C J D, Symon L, Duchen L W, Will R G. (1994) Creutzfeldt-Jakob disease and lyophilised dura mater grafts: report of two cases. J. Neurol Neurosurg Psychiat. 56:999-1000.

Gardner, D. K. (1994) Mammalian embryo culture in the absence of serum or somatic cell support. Cell Biol. Int. 18, 1163-1179

Gardner, D. K. and Lane, M. (1998a) Culture of viable human blastocysts in defined sequential serum-free media. Hum. Reprod. (suppl.) 13, 148-160

Gardner, D. K., Schooleraft, W. B., Wagley, L. et al. (1998b) A prospective randomized trial of blastocyst culture and transfer in in-vitro fertilization. Hum. Reprod. 13, 3434-3440

Green C M, Cockle S M, Watson P P et al. (1996) A possible mechanism of action for fertilization promoting peptide, a TRH-related tripeptide that promotes capacitation and fertilizing ability in mammalian spermatozoa. Mol. Reprod. Dev, 45:244-52.

Heyc, N., Henson, S., and Muller, N. (1.994) Creutzfeldt-Jakob disease and blood transfusion. Lancet 343:298299.

Kane, K T., Morgan, P. M. and Coonan, C. (1.997) Peptide growth factors and preimplantation development. Hum. Reprod. Update 3:137-157

Kemmann, E. (1998) Creutzfeldt-Jakob disease (CJD) and assisted reproductive technology (ART). Hum. Reprod. 13, 1777

Lane, M. and Gardner, D. K. (1997) Non-essential amino acids and glutamine decrease the time of the first three cleavage divisions and increase compaction of mouse zygotes in vitro. J. Assist. Reprod. Genet. 14, 398-403

Li, J., Foote, R. H., Liu, Z. et al. (1996) Development of rabbit zygotes into blastocysts in defined protein-free medium and offspring born following culture and embryo transfer. Theriogenology 47, 1103-1113

Lighten, A. D., Moore, G I., Winston, et al. (1998). Routine addition of human insulinlike growth factor-1 ligand could benefit clinical in-vitro fertilization culture. Hum. Reprod. 13, 3144-3150

Loutradis, D., Kallianidis, K., Drakkis, P. et al. (1992) Successful pregnancy in human IVF using BSA as a protein source in the transfer medium. Assist. Reprod. Technol. Androl. 3, 233-238

Mehta, T. S. and Kicssling, A. A. (1990) Development potential of mouse embryos conceived in vitro and cultured in ethylenediaminetetraacetic acid with and without amino acids or serum. Biol. Reprod. 43, 600-606

Milde, M. D. (1965). Ann. Rev. Pharmac. 5: 125

Moessner, J. and Dodson, W. C. (1993) The role of growth factors and proteins in media for in vitro fertilization. Assist. Reprod. Rev. 3, 63-67

Palermo, G., Joris, H., Devroey, P. and Van Steirteghem, A (1992) Pregnancies after intracytoplasmic injection of a single spermatozoon into oocyte. Lancet. 340:17-18

Paria, B. C. and Dey, S. K. (1990) Pre-implantation embryo development in vitro: cooperative interactions among embryos and the role of growth factors. Proc. Natl. Acad. Sci. USA, 87, 4756-4760

Paria, B. C, Tsukamura, H. and Iley, S. K. (1991) Epidermal growth factor-specific protein tyrosine phosphorylation in pre-implantation embryo development. Biol. Reprod. 45, 711-718

Parinaud, J., Milhet, P., Vieitiez, G. et al. (1998a) Human sperm capacitation and in vitro fertilization in a chemically defined and protein-free medium (SMART1). Proceedings of the 16th World Congress on Fertility and Sterility and the 54th Annual Meeting of the American Society for Reproductive Medicine. Oct. 4-9, 1998, San Francisco, Calif., United States of America, Fertil. Stern. (suppl.) p. S195-S196 (Abstract)

Parinaud, J., Vieitiez, Milhet, P., et al. (1998b) Use of plant enzyme preparation (coronase) instead of hyaluronidase for cumulus cell removal before intracytoplasmic sperm injection. Hum. Reprod. 13, 1933-1935

Poiley, S. M. (1960) A systematic method of breeder rotation for non-inbred laboratory animal colonies. Proc. Anim. Care Panel, 10, 159-166

Quinn, P. (1994) Use of co-culture with cumulus cells in insemination medium in human in vitro fertilization (IVF). J. Assist. Reprod. Genet. 11, 270-277

Saito, H., Hirayama, T., Koike, K. et al. (1994) Cumulus mass maintains embryo quality. Steril. 62, 555-558.

Schramm, R. D. and Bavister, B. D. (1996) Development of in-vitro-fertilized primate embryos into blastocysts in a chemically defined, protein-free culture medium. Hum. Reprod. 11, 1690-1697.

Serta, R. S., Sakellariou, M., Kiessling, A. A. et al. (1997) Outcome of human embryos conceived and cleaved in protein-free culture conditions. Proceedings of the 53$^{rd}$ Annual Meeting of the American Society for Reproductive Medicine. October 1.

Stewart G J, Wang Y, Niewiarowski S. (1995) Methylcellulose protects the ability of anchorage-dependant cells to adhere following isolation and holding in suspension. Biotechniques. 19(4):598-604

Meeting of the American Society for Reproductive Medicine. October 188-22, 1997, Cincinnati, Ohio, United States of America, (suppl.) 5214-5215 (Abstract)

Spindle, A. (1995) Beneficial effect of taurine on mouse zygotes developing in protein-free culture medium. Theriogenology 44, 761-772

Staessen, C., Janssenswillen, C., De Clerck, E. et al. (1998) Controlled comparison of commercial media for human in-vitro fertilization: Menezo B2 medium versus Medi-Cult universal and BM1 medium. Hum. Reprod. 13, 2548-2554

Tesarik, J., Pilka, L., Drahorad, J. et al. (1988) The role of cumulus cell-secreted proteins in the development of human sperm fertilizing ability: implications in 1VF. Hum. Reprod. 3, 129-132

Parainaud, J., Milhet, P., Vieitez, G. and Richoilley, G. (1999). Use of a medium devoid of 5 any human or animal compound (SMART2T) for embryo culture in intracytoplasmic sperm injection. J. Assist. Reprod. Genet. 16: 13-16.

Truyen, U., Parrish, C. R., Harder, T. C. et al. (1995) There is nothing permanent except change. The emergence of new viral diseases. Vet. Microbiol. 43, 103-122. Cited in: Parinaud et al., 1998b Van Os, H. C., Drogendijk, Aat, C. Fetter, W. P. F. et al. (1991) The influence of contamination of culture medium with hepatitis B virus on the outcome of in vitro fertilization pregnancies. Am. J. Obstet. Gynecol. 165, 152-159

Vidlakova, Erazimova, J., Horky, J. et al. (1972) Relationship of serum antioxidative activity to tocopherol and serum inhibitor of lipid peroxidation, Chim. Acta 36, 61-66

Wayner, Dam, Burton, G. W., Ingold, K. U. et al. (1987) The relative contribution of vitamin F, mate, ascorbate and proteins to total peroxyl radical-trapping antioxidant activity of human blood plasma. Biochim. Biophys. Acta 924, 408-419

Widdowson, E. M. and Dickerson, J. W. T. (1964). In: Comar, L. C. and Brommer, F. (eds.), Mineral Metabolism, New York—London, Vol. IIA, p. 13.

I claim:

1. A substantially protein-free cell culture medium for human reproductive cells, suitable for use throughout in vitro treatment of human reproductive cells to be used in vitro fertilization and other assisted reproduction technologies, comprising mineral salts, amino acids, antioxidants, vitamins, nutrients, antibiotics, D-mannitol, and methylcellulose that has a molecular weight of 14,000 Daltons.

2. The substantially protein-free medium according to claim 1, wherein said methylcellulose is characterized so that a 2% solution has a viscosity of 15 centipoise at 25° C.

3. The substantially protein-free medium according to claim 1, wherein said methylcellulose is of formula I:

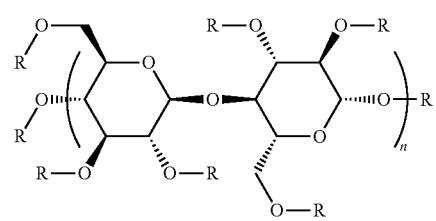

wherein each R is independently H or $CH_3$ and n is an integer having a value from 34 to 43 and wherein methoxy substitution is from 27.5% to 31.5% by weight.

4. The substantially protein-free medium according to claim 3, wherein the average number of $CH_3$ substituents attached to each sugar moiety of the compound of formula I is 1.5 to 1.9.

5. The substantially protein-free medium according to claim 1, 2, 3, or 4, wherein said methylcellulose is present in the solution at a concentration from 0.01 g/L to 0.5 g/L.

6. The substantially protein-free medium according to claim 1, 2, 3, or 4, wherein said methylcellulose is present in the solution at a concentration from 0.01 g/L to 0.15 g/L.

7. The substantially protein-free medium according to claim 1, 2, 3, or 4, wherein said methylcellulose is present in the solution at a concentration of 0.1 g/L.

8. The substantially protein-free medium according to claim 1, 2, 3, or 4, wherein the amino acids are L-arginine, L-cystine, L-histidine, L-isoleucine, L-leucine, L-lysine, L-methionine, L-phenylalanine, L-threonine, L-tryptophan, L-tyrosine, L-valine, L-alanine, L-taurine, L-glutamic acid, L-glutamine or glycine, or any combination thereof.

9. The substantially protein-free medium according to claim 8, wherein the amino acids are present at concentrations between: 0.018 mM and 0.18 mM for L-arginine HCl; 0.0025 mM and 0.025 mM for L-cystine.2HCl; 0.005 mM and 0.05 mM for L-histidine HCl.H$_2$O; 0.01 mM and 0.1 mM for L-isoleucine; 0.01 mM and 0.1 mM for L-leucine; 0.0125 mM and 0.125 mM for L-lysine.HCl; 0.0025 mM and 0.025 mM for L-methionine; 0.005 mM and 0.05 mM for L-phenylalanine; 0.01 mM and 0.1 mM for L-threonine; 0.00125 mM and 0.0125 mM L-tryptophan; 0.005 mM and 0.05 mM L-tyrosine.2Na2H$_2$O; 0.01 mM and 0.1 mM for L-valine; 1.0 mM and 10 mM for L-alanine; 1.0 mM and 30 mM for L-taurine; 0.01 mM and 1.0 mM for glutamic acid; 1.0 mM and 50 mM for L-glutamine or 0.1 mM and 1.0 mM for L-glycine.

10. The substantially protein-free medium according to claim 9, wherein the amino acids are present at a concentration of: 0.5 mM L-arginine; 0.01 mM L-cystine.2HCl; 0.02 mM L-histidine, 0.04 mM L-isoleucine; 0.04 mM L-leucine; 0.05 mM L-lysine.HCl; 0.01 mM L-methionine; 0.02 mM L-phenylalanine; 0.04 mM L-threonine; 0.005 mM L-tryptophan; 0.02 mM L-tyrosine.2Na2H$_2$O; 0.04 mM L-valine; 0.5 mM L-alanine; 20 mM for L-taurine; 0.5 mM glutamic acid; and 20 mM L-glutamine or 0.25 mM L-Glycine.

11. The substantially protein-free medium according to claim 1, 2, 3, or 4, wherein the mineral salts comprising the medium are calcium chloride, magnesium sulfate, potassium chloride, sodium chloride and sodium phosphate.

12. The substantially protein-free medium according to claim 11, wherein the mineral salts comprising the medium are present at concentrations between: 3.0 mM and 3.6 mM for calcium chloride; 0.7 mM and 0.81 mM for magnesium sulfate; 4.7 mM and 5.4 mM for potassium chloride; 0.1 M and 0.12 M for sodium chloride; and 0.89 mM to 1.0 mM for sodium dihydrogen phosphate.

13. The substantially protein-free medium according to claim 12, wherein the mineral salts comprising the medium are present at a concentration of: 3.1 mM for calcium chloride; 0.72 mM for magnesium sulfate; 4.8 mM for potassium chloride; 0.11 M for sodium chloride; and 0.88 mM for sodium dihydrogen phosphate.

14. The substantially protein-free medium according to claim 1, 2, 3, or 4, wherein the vitamins comprising the medium are choline chloride, myoinositol, niacinamide, D-pantothenic acid, pyridoxine HCl, riboflavin, thiamine HCl, folic acid, vitamin B12, vitamin E, or any combination thereof.

15. The substantially protein-free medium according to claim 14, wherein the vitamins comprising the medium are present at concentrations between: 0.004 mM and 0.005 mM for choline chloride; 0.0024 mM and 0.0028 mM D-biotin; 0.0067 mM and 0.0078 mM for myoinositol; 0.005 mM and 0.0057 mM for niacinamide; 0.0025 mM and 0.003 mM for D-pantothenic acid; 0.003 mM and 0.0034 mM for pyridoxine HCl; 0.00016 mM and 0.00019 mM for riboflavin; 0.0018 mM and 0.0021 mM for thiamine HCl; 0.0014 mM and 0.0016 mM for folic acid; 443 pM and 885 pM for vitamin B12; and 0.008 mM and 0.012 mM for vitamin E.

16. The substantially protein-free medium according to claim 15, wherein the vitamins comprising the medium are present at a concentration of 0.004 mM for choline chloride; 0.0024 mM D-biotin; 0.0067 mM for myoinositol; 0.005 mM for niacinamide; 0.0025 mM for D-pantothenic acid; 0.003 mM for pyridoxine HCl; 0.00016 mM for riboflavin; 0.0018 mM for thiamine HCl; 0.0014 mM for folic acid; 616 pM for vitamin B12; and 0.010 mM vitamin E.

17. The substantially protein-free medium according to claim 1, 2, 3, or 4, wherein the nutrients comprising the medium are D-glucose, pyruvate, fructose, sodium lactate, or any combination thereof.

18. The substantially protein-free medium according to claim 17, wherein the nutrients comprising the solution are present at a concentration of 4.2 mM and 5.6 mM for D-glucose; 0.3 mM for sodium pyruvate; 1 mM and 5.6 mM for fructose; and 10 mM for sodium lactate.

19. The substantially protein-free medium according to claim 18, wherein D-glucose is present at a concentration of 4.3 mM.

20. The substantially protein-free medium according to claim 19, wherein fructose is present at a concentration of 5.1 mM.

21. The substantially protein-free medium according to claim 1, wherein the antioxidant in the solution is glutathione.

22. The substantially protein-free medium according to claim 21, wherein the concentration of glutathione is between 0.25 mM and 0.35 mM.

23. The substantially protein-free medium according to claim 22, wherein the concentration of glutathione is 0.3 mM.

24. The substantially protein-free medium according to claim 1, 2, 3, or 4, further comprising EDTA.

25. The substantially protein-free medium according to claim 24, wherein the concentration of EDTA is between 0.1 mM and 0.103 mM.

26. The substantially protein-free medium according to claim 25, wherein the concentration of EDTA is 0.1 mM.

27. The substantially protein-free medium according to claim 1, 2, 3, or 4, further comprising HEPES.

28. The substantially protein-free medium according to claim 27, wherein the concentration of HEPES is 15 mM or 25 mM, and the concentration of D-glucose is between 4.2 mM to 5.6 mM.

29. The substantially protein-free medium according to claim 1, 2, 3, or 4, further comprising phenol red or other pH indicator.

30. The substantially protein-free medium according to claim 29, wherein the concentration of phenol red is 0.031 mM.

31. The substantially protein-free medium according to claim 1, 2, 3 or 4, wherein gentamycin sulfate is present in the solution at a concentration from 1.5 g/L to 4 g/L.

32. The substantially protein-free medium according to claim 1, 2, 3 or 4, wherein Penicillin G is present in a concentration of 75 g/L.

33. The substantially protein-free medium according to claim 1, 2, 3, or 4, wherein D-mannitol is present at a concentration from 0.056 micromolar to 6.9 micromolar.

34. The substantially protein-free medium of claim 33, wherein D-mannitol is present at a concentration of 2.8 micromolar.

35. The substantially protein-free medium of claim 1, 2, 3, or 4, further comprising sodium bicarbonate.

36. The substantially protein-free medium of claim 35, wherein sodium bicarbonate is present at a concentration of 26.2 mM.

37. The substantially protein-free medium of claim 35, wherein sodium bicarbonate is present at a concentration of between 4.0 mM and 26.2 mM.

38. A method comprising the step of contacting human reproductive cells in vitro with the substantially protein-free culture medium of claim 36.

39. The method according to claim 38, wherein the human reproductive cell is an unfertilized ovum.

40. The method according to claim 38, wherein the human reproductive cell is a plurality of spermatozoa.

41. The method according to claim 38, wherein the human reproductive cell is a fertilized ovum.

42. A substantially protein-free cell culture medium for human reproductive cells, suitable for use throughout in vitro treatment of human reproductive cells to be used in vitro fertilization and other assisted reproduction technologies, comprising 0.1 g/L methylcellulose having a molecular weight of 14,000 Daltons; 0.06 mM L-arginine; 0.01 mM L-cystine.2HCl; 0.02 mM L-histidine, 0.04 mM L-isoleucine; 0.04 mM L-leucine; 0.041 mM L-lysine.HCl; 0.01 mM L-methionine; 0.019 mM L-phenylalanine; 0.04 mM L-threonine; 0.0049 mM L-tryptophan; 0.02 mM L-tyrosine.2Na2H$_2$O; 0.039 mM L-valine; 0.5 mM L-alanine; 20 mM for L-taurine; 0.39 mM glutamic acid; 20 mM L-glutamine; 0.25 mM L-Glycine; 1.67 mM calcium chloride; 0.57 mM magnesium sulfate; 3.76 mM potassium chloride; 0.084 M sodium chloride; 0.7 mM for sodium dihydrogen phosphate; 0.004 mM choline chloride; 0.0024 mM D-biotin; 0.0067 mM myoinositol; 0.005 mM niacinamide; 0.0028 mM D-pantothenic acid; 0.003 mM pyridoxine HCl; 0.00016 mM riboflavin; 0.002 mM (0.0006 g/L) thiamine HCl; 0.0014 mM folic acid; 100 µl/L vitamin B12; 333 µl/L vitamin E; 4.1 mM D-glucose; 0.27 mM sodium pyruvate; 5.1 mM fructose; 1.9 ml/L sodium lactate; 0.3 mM glutathione; 0.1 mM EDTA; 0.022 mM phenol red; 0.0911 g/L D-mannitol; 26.2 mM sodium bicarbonate; and 75 g/L Penicillin G and 1.5 g/L gentamycin sulfate; or 4 g/L gentamycin sulfate.

43. The substantially protein-free culture medium of claim 42, wherein the concentration of gentamycin sulfate is 4 g/L.

44. The substantially protein-free cell culture medium of claim 42, wherein the concentration of D-glucose is 4.1 mM and further comprising 15 mM HEPES.

45. The substantially protein-free cell culture medium of claim 42, wherein the concentration of D-glucose is 4.1 mM and further comprising 25 mM HEPES.

46. The substantially protein-free cell culture medium of claim 43, wherein the concentration of D-glucose is 4.1 mM and further comprising 15 mM HEPES.

47. The substantially protein-free cell culture medium of claim 43, wherein the concentration of D-glucose is 4.1 mM and further comprising 25 mM HEPES.

48. The substantially protein-free culture medium of claim 42, wherein the concentration of Penicillin G is 75 g/L and the concentration of gentamycin sulfate is 1.5 g/L.

49. The substantially protein-free cell culture medium of claim 48, wherein the concentration of D-glucose is 4.1 mM and further comprising 15 mM HEPES.

50. The substantially protein-free cell culture medium of claim 48, wherein the concentration of D-glucose is 4.1 mM and further comprising 25 mM HEPES.

\* \* \* \* \*